(12) United States Patent
Häberlein

(10) Patent No.: US 6,344,740 B1
(45) Date of Patent: Feb. 5, 2002

(54) GUIDE DEVICE FOR TESTING ELONGATED OBJECTS

(75) Inventor: Peter Häberlein, Reutlingen (DE)

(73) Assignee: Institut Dr. Friedrich Forster Prufgeratebau GmbH & Co. KG, Reutlingen (DE)

( * ) Notice: Subject to any disclaimer, the term of this patent is extended or adjusted under 35 U.S.C. 154(b) by 0 days.

(21) Appl. No.: 09/318,157

(22) Filed: May 25, 1999

(30) Foreign Application Priority Data

May 25, 1998 (DE) .......................................... 198 22 986

(51) Int. Cl.[7] .......................... G01N 27/87; G01N 27/72
(52) U.S. Cl. .......................... 324/226; 324/262
(58) Field of Search .................................. 324/226, 262, 324/238, 225, 206; 242/157 R, 171

(56) References Cited

U.S. PATENT DOCUMENTS

| | | | |
|---|---|---|---|
| 3,640,123 A | 2/1972 | Vogt et al. | 73/71.5 |
| 4,629,991 A * | 12/1986 | Wheeler | 324/262 |
| 5,412,319 A | 5/1995 | Ciani | 324/241 |
| 5,520,347 A * | 5/1996 | Bass et al. | 242/171 |
| 5,744,955 A | 4/1998 | Booker | 324/240 |

FOREIGN PATENT DOCUMENTS

| | | |
|---|---|---|
| DE | 40 07 471 A1 | 9/1991 |
| DE | 43 11 566 A1 | 10/1994 |

* cited by examiner

*Primary Examiner*—Walter Snow
(74) *Attorney, Agent, or Firm*—Duane Morris, LLP

(57) ABSTRACT

A guide device for linear guidance of elongated objects, particularly for positioning wires passing a nondestructive eddy current test device, can be the inlet nozzle or outlet nozzle, and has a brush arrangement integrated into a guide sleeve. The brush arrangement damps vibration of the wires or other elongated objects transiting the test device. A wire guided by the guide device is protected at its surface and subjected to little or no transverse vibration in the vicinity of the test probe of the test device, resulting in improved measurement accuracy.

28 Claims, 2 Drawing Sheets

GUIDE DEVICE FOR TESTING ELONGATED OBJECTS

Figure 1:
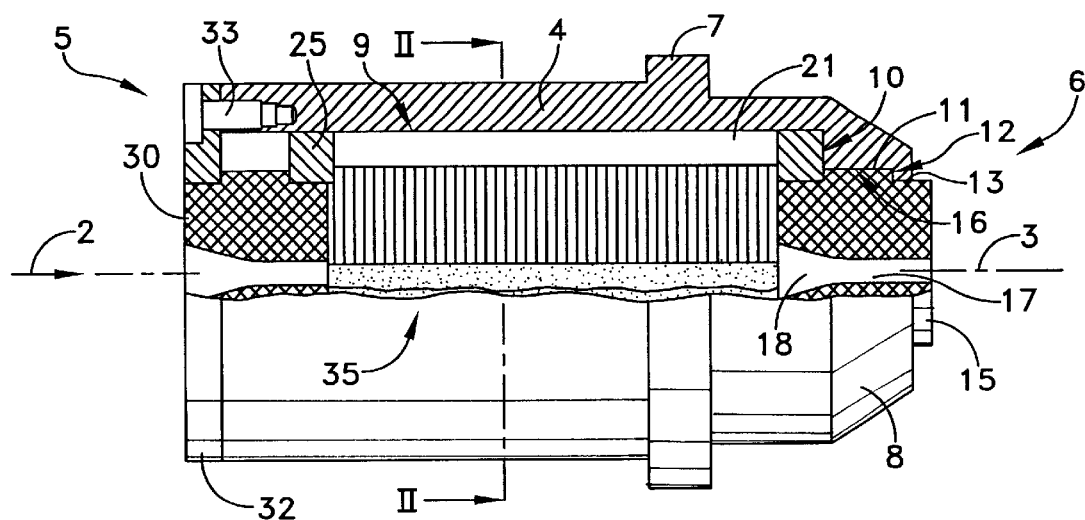

The invention relates to a guide device for guiding elongated objects, particularly wires, which are movable in a passage direction along a passage axis relative to the guide device.

Elongated objects, such as metal wires, rods, bars or tubes, can be starting materials for high-value end products and are frequently subject to the highest quality requirements. Tests for surface defects are an important part of the quality control for such products. One objective is inter alia an uninterrupted and complete testing or inspection of the surfaces with high resolution, even for small defects, e.g. cracks, preferably in the cycle and speed of the manufacturing process. Nowadays such tests are frequently carried out using magnetic methods, particularly eddy current technology performed on a continuous basis, in which the object to be tested or inspected is guided at high speed through an axial test section of a test device e.g. equipped with a rotary test head with eddy current probes and the probes test the surface of the object, preferably in contactless manner.

In the passage direction upstream of the area of the test probes, such a test device normally has a so-called inlet nozzle and behind it an outlet nozzle. These guide devices, also known as protective nozzles fulfil a double function. They protect the test heads against damage, particularly during the entry and exit of the test material. They also limit the maximum eccentricity of the moving test material within the test section to a narrow, confined amount, within which the spacing compensation of the test device can cancel out the sensitivity fluctuations strongly dependent on the spacing between the test object surface and the test probe.

A guide nozzle known from DE 40 07 471 has for the damping of vibrations of the transiting objects a damping device with three guide elements directed onto the surface of the object and whereof each has a sliding body with wear-resistant surface for sliding contact with the test product and which is carried by a damping member made from a rubber-like material. Such test devices generally operate in a completely satisfactory manner.

However, particularly in the case of high passage or transit speeds and very thin, transiting testpieces, such as e.g. highly polished wires for the medical sector with diameters of approximately one or a few mm, very high disturbance levels have been observed, which impair the measuring accuracy. In addition, the metallic sliding bodies can damage sensitive surfaces.

The problem of the invention is to propose a guide device making it possible to increase the measuring accuracy of in particular test devices operating in contactless manner in the case of gentle material guidance.

According to the invention this problem is solved.

A guide device according to the invention can in particular be used with advantage in a test device for the preferably magnetic, non-destructive testing of elongated objects in a continuous process. It has a damping device for damping vibrations, particularly transverse vibrations of the transiting objects. The damping device has a plurality of elastic damping members for direct, preferably sliding contact with the transiting object and which are able to absorb vibration energy.

Such damping members acting directly on the test product and whereof there can be 10, 50, 100 or 1000, absorb vibration energy at numerous points, particularly in the range of maximum transverse deflection, i.e. in the area of a vibration antinode and have a damping counteracting effect on the object deflection. A large number of damping members can lead to each individual damping member acting on the test product only exerting a limited pressure force on the test product surface, so that the test product can be guided in a gentle manner. An advantageously statistical distribution of the damping members assists a damping in a wide, continuous vibration frequency spectrum. It has been found that in particular in the case of thin wires tested at high passage speeds wire vibrations can occur in the vicinity of the test probes, which give rise to high disturbance levels for the test signals and therefore impair the measuring accuracy, especially for the detection of small defects. A guide device with the inventive damping device guiding in surface-protecting manner can counteract such vibrations and ensure a particularly quiet running, with no or only limited transverse vibrations, of the test material in the vicinity of the test probes.

In a preferred embodiment, the damping device has a brush arrangement and is in particular formed by the latter. The bristles or fibers of a brush arrangement can engage in gently sliding manner on a transiting object and form the damping members. Vibrations of the object lead to a deflection, particularly a bending of fibers and/or a rubbing against one another of adjacent fibers deflected to a varying degree. Both the substantially elastic fiber bending and also the reciprocal rubbing of fibers require energy, which is deducted from a vibration of the object, so that its vibration is damped. Flexible bristles engaging gently on the guided object also facilitate the introduction and passage of the objects to be guided into or through the guide device and only very limited friction losses occur.

In addition to the damping action, a brush arrangement can also be used for cleaning a transiting object and/or it can act in the manner of a brush seal as a sealing device and seal the axial area following in the damping device transit direction against the introduction of dirt.

As a result of the flexibility of the bristle fibers, a single brush arrangement of given dimensions can be used for test objects of different diameters from an appropriate diameter range. There is an automatic diameter adaptation of the damping device in that, in accordance with the thickness of the transiting object, the bristle fibers are deflected or bent to a greater or lesser extent. Thus, it is e.g. possible to create guide devices with nominal sizes or internal diameters of e.g. between 1 mm and approximately 130 to 140 mm, each guide device with a brush arrangement being able to cover a certain diameter range of e.g. between 1 and 10 mm, particularly between 2 and 5 mm range width. A test device suitable for different diameters consequently only requires far fewer guide devices of this type than one having conventional guide devices.

As a function of the intended use the fibers can be hard or soft, thick or thin, more or less flexible, bending-resistant, buckling-resistant and/or abrasion-resistant. Thus, the fibers can be wire, synthetic or natural fibers. For guiding thin, particularly superfinished wires for the medical sector or other test objects having sensitive surfaces soft natural or synthetic fibers having a good sliding action on metals have proved very satisfactory. A brush arrangement can also have a uniform or statistical mixture of several different fibers or fiber types.

A brush arrangement can e.g. have at least one circular brush with e.g. substantially radially inwardly directed bristles. A preferred embodiment is characterized in that the brush arrangement has at least one and preferably several axially directed strip brushes distributed more particularly in symmetrical manner around the guide device surface. It is e.g. possible to provide three strip brushes in each case mutually displaced in the circumferential direction by 120° and whose bristles define with their free ends an e.g. triangular passage for a transiting object. A circumferentially symmetrical arrangement of vibration-damping fibers with their free ends oriented radially and partly tangentially to the test object has proved to be particularly advantageous for vibration damping purposes. In addition, an improved centering of the transiting objects compared with conventional guide nozzles has been observed.

A format or diameter change is more particularly facilitated in a preferred embodiment in that the damping members or the at least one brush of the brush arrangement is fixed, preferably without tools, in detachable manner to a preferably sleeve-like brush support. A brush, which normally has a brush body, which carries the fibers or bristles, can in particular be inserted in the brush support, which makes a format or size change particularly simple.

Particularly good vibration damping can be achieved if the damping device has an active axial length which can be brought into contact with the transiting object and which represents a multiple, preferably 10 to 100 times, particularly approximately 30 times the diameter of the transiting object. A suitable, not excessively short length of the damping device is particularly suitable for damping different frequencies of a vibration spectrum.

In the axial direction, a damping device can be positioned upstream and/or downstream of the associated guide device. In a preferred embodiment the damping device is completely arranged in protective manner in the interior of the guide device casing or is integrated into the same. The guide device can have a front guide bush, upstream of the damping device and provided with a preferably cross-sectionally circular, axial passage opening, which is preferably widened in funnel-shaped manner on the inlet side. The object to be guided can be passed centrally through this passage opening into the interior of the damping device. A preferably provided, rear guide bush can follow the damping device and in particular in conjunction with the front guide bush can prevent a tilting of the transiting object in the guide device. The guide bushes can be shaped in the manner of drawing dies and/or are preferably made from wear-resistant hard metal. To prevent surface damage to the transiting material, preferably the inner face of the passage opening of a guide bush is highly polished at least in the area through which the object passes. A particularly inexpensive, simple construction of a guide device is obtained if the front and rear guide bushes have an identical construction.

According to a preferred embodiment, the first guide bush and/or the second guide bush are fixed detachably to a preferably sleeve-like casing of the guide device. A detachable fastening, which can e.g. be secured by screws, facilitates the replacement of guide sleeves with different passage opening diameters for adaptation to objects having different cross-sections, without it being necessary to replace the casing optionally fitted into a test device. Without separate fastening means such as screws or the like having to be provided for it, the damping device can be held in axially clearance-free manner and can optionally be axially fixed between the front guide bush and the rear guide bush.

The invention makes it possible to provide a test device operating with high measuring accuracy for preferably magnetic, non-destructive testing of elongated objects, particularly wires, in a continuous process. At least one test probe can operate in an axial test section of the test device. A test device according to the invention is characterized in that in the passage direction upstream and/or downstream of the axial test section is provided at least one guide device of the described type. Preferably the guide device is used in conjunction with a test probe, particularly an eddy current probe operating in contactless manner and which is constructed as a rotary probe or feed-through coil. Use with other, particularly magnetic testing methods, e.g. the stray flux method is also advantageous. Test objects running in a central, quiet and vibration-free manner are also advantageous in testing methods with test probes contacting the test object.

It has proved particularly advantageous for an axial spacing between the test probe and test device to be short, the axial spacing preferably being less than 10 mm, particularly between 0.5 and 2 mm. Such a close arrangement of a vibration-damping, protecting guide device upstream and/or downstream of the test probes ensures that no vibrations occur again between the guide device and the test probe section which could impair the measurement.

These and further features can be gathered from the claims, description and drawings and the individual features, both singly and in the form of sub-combinations, can be implemented in an embodiment of the invention and in other fields and can represent advantageous constructions.

An embodiment of the invention is described in greater detail hereinafter relative to the attached drawings, wherein show:

FIG. 1 A part sectional side view of an embodiment of an inventive guide device from a direction perpendicular to the passage direction of an elongated object.

Figure 2:
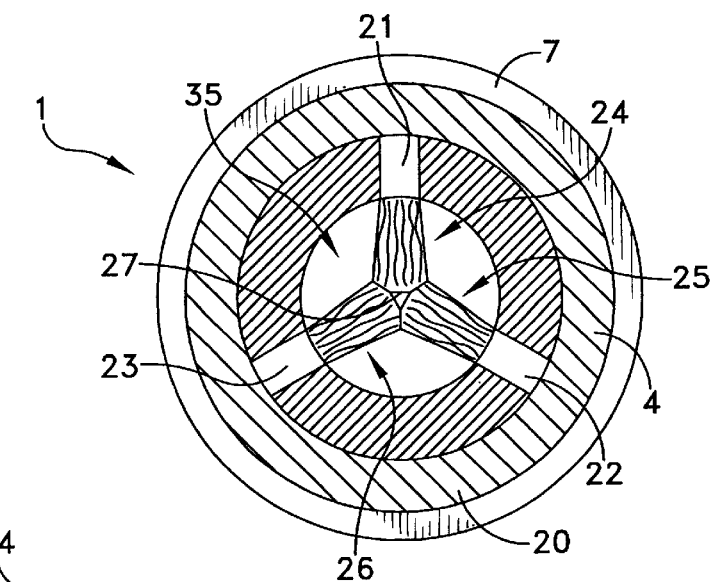

FIG. 2 A cross-section perpendicular to the passage axis along line II—II in FIG. 1.

Figures 3A, 3B:
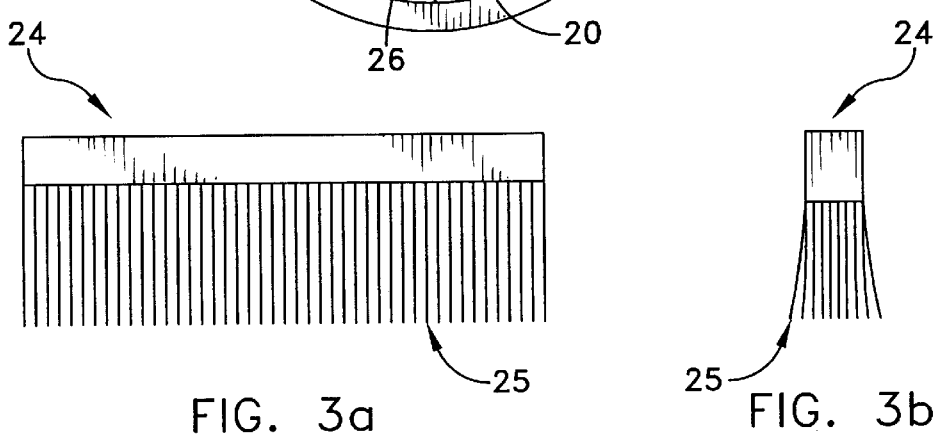

FIG. 3 A side view (a) and an axial front view (b) of a damping device strip brush insertable in the guide device.

Figure 4:
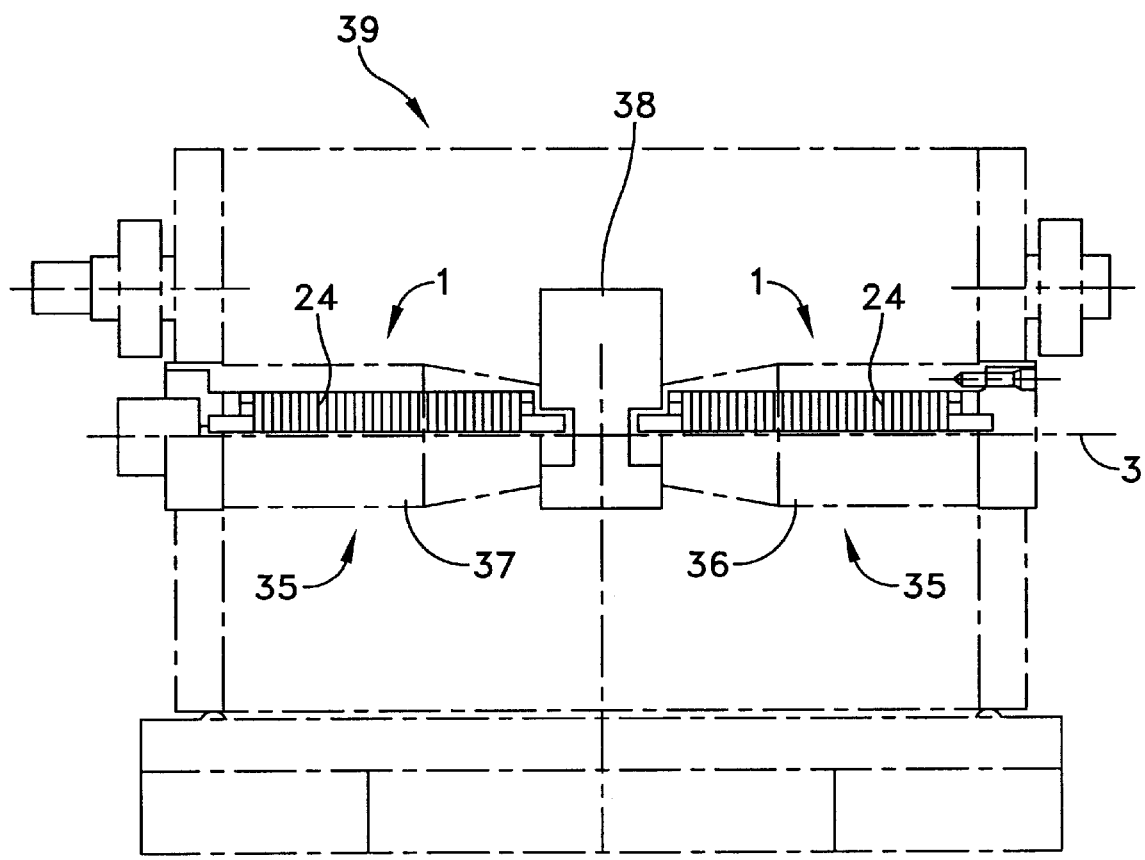

FIG. 4 A schematic side view of a test device provided with embodiments of guide devices upstream and downstream of a test probe.

The part sectional side view of FIG. 1 shows a preferred embodiment of a guide device 1 according to the invention and which is constructed in such a way that an elongated object, e.g. a wire with a diameter of approximately 2 mm, can pass through the guide device in a passage direction 2 along a passage axis 3. The guide device I can be used in place of conventional inlet or outlet nozzles on per se known, particularly magnetic test devices, e.g. on a test device with an eddy current rotary head, being replaceably fitted e.g. by means of a bayonet catch.

The guide device 1 constructed as a guide sleeve has a sleeve-like, metallic casing 4, which on the inlet side 5 is roughly cylindrical, has between the inlet side and outlet side 6 a flange-like collar 7 for fixing the guide sleeve to the test device and on the outlet side beyond the collar terminates in a frustum-shaped end portion 8. The interior of the casing 4 has an inlet side, cylindrical portion 9, a smaller diameter, cylindrical portion 11 connected thereto and accompanied by the formation of a radial, inner step 10 and a cylindrical end portion 13 connected thereto and accompanied by the formation of a radial, inner step 12.

An outlet side, rear guide bush 15 made from hard metal has a terminally, substantially cylindrical shape with a radially outwardly projecting collar 16 centrally located between the end faces and whose external diameter substantially corresponds to the internal diameter of the cylindrical portion 11. The guide sleeve 15 is inserted in the end portion 8 in such a way that on the outlet side it projects with a cylindrical portion out of the cylindrical portion 13 of the casing. In the fitted state, the guide bush 15 has an axial through opening 17 aligned with the passage axis 3 and which on the outlet side is substantially cylindrical with a diameter of e.g. 2 mm and is widened on the inlet side, accompanied by the formation of a trumpetlike widening insertion funnel with gently curved internal radius. The inside of the passage opening 17 is highly polished and free from edges or corners, so that a transiting object on contact is not damaged by the guide bush, e.g. scratched. In normal operation between the inner face of the passage opening and the test object there is an air gap of e.g. 1/100 mm radial width.

Towards the inlet side 5 to the rear guide bush 15 is connected a bush or sleeve-like brush support 20, whose cylindrical external circumference is such that it can be axially inserted in clearance-free manner in the cylindrical opening 9 of the casing until its outlet side end face engages on the collar 16 of the rear guide sleeve 15 and axially fixes the same. As can be seen in FIG. 2, the metallic brush support 20 has three, radially through longitudinal slots 21, 22, 23, circumferentially mutually displaced by in each case 120° and which, as shown in FIG. 1, do not extend up to the front ends of the sleeve 20.

In each of the longitudinal slots is radially inserted an axially directed strip brush 24, 25, 26 in such a way that the bristles or fibers are raised substantially radially and some approximately tangentially to the passage axis 3. As can be seen in FIG. 3, the free ends of the fibers of each of the strip brushes form a macroscopic, substantially planar brush face 25, in which are located the free ends of the flexible natural fibers of the brush. The length of the fibers is such that in the case of strip brushes inserted in the longitudinal slots up to radial external engagement on the casing 9, the free ends of the strip brushes arranged in Mercedes star-like manner define an approximately triangular passage cross-section 27. The cross-sectionally triangular passage channel 27 has internal diameters smaller than the diameter of the wire passed through, so that when the wire is passed through at least part of the bristles acting as damping members and guide elements are slightly bent in the passage direction and/or transversely thereto and exerts a limited pressure force on the object passed through predetermined by the fiber tension.

Following the insertion of the rear guide bush 15 and the insertion of the replaceable strip brushes in the associated longitudinal slots, the sleevelike brush support 20 is axially introduced into the casing 9 until it strikes against the guide bush 15. Then, the front guide bush 30, identical to the rear guide bush 15, is inserted in a front, cylindrical opening of the sleeve 20 until the collar 31 engages on the sleeve 20. The overall arrangement is axially fixed by a disk-like end plate 32 mounted on the insertion side end of the casing 9 and which is frontally screwed down on the casing by means of several fastening screws 33 distributed round the guide device circumference.

The described assembly of the guide device by simply fitting in appropriately matched parts permits an easy replacement of the guide bushes and/or brush arrangement, by merely unscrewing the end plate 32, extracting the inserted parts from the interior of the casing 9 and the insertion of other parts with a larger or smaller passage diameter in the described order into the sleeve 9 and fixing by screwing down the plate 32. In the case of a diameter change within a diameter range of e.g. 5 to 10 mm covered by the diameter range of a brush arrangement, it is merely necessary to replace the guide bushes.

The guide device provided with a damping device 35 in the form of a brush arrangement 20, 24, 25, 26 functions as follows. Initially, preferably in the disassembled state of the guide device, by corresponding fitting of diameter-adapted guide sleeves and a corresponding brush arrangement it is prepared for the object diameter to be tested or inspected. The guide device is then fixed as an inlet nozzle to a test device using the collar 7. On the outlet side is preferably fixed an identical guide sleeve with the same orientation. The object to be tested is passed along the passage axis 3 through the guide sleeve 1 and with the test device operating is passed through the latter. The insertion and passage are very simple as a result of the flexibility of the fibers, which gently side on the surface of the inserted object and no wire bending is possible. The object passed through in the vicinity of the triangular passage channel 27 arranged coaxially to the axis 3 bends part of the brush arrangement fibers coming into sliding contact therewith to a limited extent in the passage direction and/or transversely thereto, so that the entire brush arrangement is placed round the test object and holds and guides the latter centrally in the vicinity of the axis 3. The fibers form a more or less static distribution of elastic damping members, which engage radially or tangentially on the object passing through and bend to a greater or lesser extent in the case of transverse vibrations of the object.

The vibration-induced bending of the brush fibers normally differs for neighbouring fibers, so that they move slidingly against one another and rub on one another. The friction of the fibers in conjunction with the substantially elastic bending of the fibers leads to an absorption of the vibration energy and consequently to the damping of possibly occurring transverse vibrations. The latter are prevented or substantially reduced in that each transverse vibration must produce an energy-absorbing bending and/or rubbing of the fibers on one another. Although the vibration-damping, radial overall force exerted on the object by the brush arrangement can be considerable, each individual fiber in contact with the object only exerts a limited force on the outside of the transiting object. Particularly when using soft fibers, e.g. natural fibers, the damping action can be attained without there being any surface damage of the optionally highly sensitive surfaces.

In the case of a damped guide device in the manner of the damped guide sleeve 1 not only is a dimensional accuracy-aiding damping device created, but simultaneously a mechanical cleaning device for the test product entering in the vicinity of the test probes. As a result the disturbance level of the measurement can be reduced and consequently the measuring accuracy increased. The measuring accuracy is also improved in that the inventive guide devices center particularly well the objects passed through in the clearance area of the hard metal guide bushes, so that any surface-damaging contact with the guide bushes can be reduced or avoided.

The use of inventively constructed guide sleeves as the inlet nozzle 36 arranged upstream of a test probe 38 and/or nozzle 37 arranged downstream of a test probe 38 for a test device 39 (as shown schematically in FIG. 4) provides a very inexpensive, simple, but effective possibility of increasing measuring accuracy in virtually all conventional test devices operating in a continuous process, particularly those having contactless test probes.

What is claimed is:

1. Guide device for guiding elongated objects to be tested in a test device for material testing, the elongated objects being movable at high speed in a passage direction along a passage axis relative to the guide device, the guide device comprising structure for mounting the guide device in the test device, and a damping device for damping vibrations of the elongated objects transiting the guide device, wherein the damping device has a plurality of elastic damping members adapted for contacting the elongated objects passing through the guide device.

2. Guide device for guiding objects which are movable in a passage direction along a passage axis relative to the guide device, the guide device comprising a damping device for damping vibrations of the elongated objects transiting the guide device, wherein the damping device has a plurality of elastic damping members adapted for contacting the elongated objects passing through the guide device, wherein the damping device comprises at least one of more than 10 and more than 100 damping members.

3. Guide device according to claim 1, wherein the damping members are statistically distributed.

4. Guide device for guiding elongated objects which are movable in a passage direction along a passage axis relative to the guide device, the guide device comprising a damping device for damping vibrations of the elongated objects transiting the guide device, wherein the damping device has a plurality of elastic damping members adapted for contacting the elongated objects passing through the guide device, wherein the damping device comprises a brush arrangement with a plurality of brush fibers, wherein the brush fibers form the damping members.

5. Guide device according to claim 1, wherein the damping members are oriented such that they extend at least one of substantially radially and substantially tangentially to the passage axis.

6. Guide device according to claim 1, wherein the damping members are substantially made from a non-metallic material.

7. Guide device according to claim 6, wherein the damping members comprise at least one of synthetic and natural fibers.

8. Guide device according to claim 4, wherein the brush arrangement comprises at least one strip brush oriented substantially parallel to the passage axis.

9. Guide device according to claim 4, wherein the brush arrangement comprises a plurality of strip brushes being oriented parallel to the passage axis and being distributed around the circumference of the guide device.

10. Guide device according to claim 1, wherein the guide device comprises a sleeve-like support and wherein the damping members are detachably fixed to the sleeve-like support.

11. Guide device according to claim 10, wherein the damping members and the sleeve-like support are adapted for fixing the damping members to the sleeve-like support without using tools.

12. Guide device according to claim 1, wherein the damping device has an effective axial length wherein the damping device can be brought into contact with the elongated object, wherein the effective axial length is between 10 and 100 times the diameter of the elongated objects transiting the guide device.

13. Guide device for guiding elongated objects which are movable in a passage direction along a passage axis relative to the guide device, the guide device comprising a damping device for damping vibrations of the elongated objects transiting the guide device, wherein the damping device has a plurality of elastic damping members adapted for contacting the elongated objects passing through the guide device, wherein the guide device comprises a casing defining an interior of the casing and wherein the damping device is completely located in the interior of the casing.

14. Guide device for guiding elongated objects which are movable in a passage direction along a passage axis relative to the guide device, the guide device comprising a damping device for damping vibrations of the elongated objects transiting the guide device, wherein the damping device has a plurality of elastic damping members adapted for contacting the elongated objects passing through the guide device, wherein the guide device comprises at least one of a front guide bush disposed upstream of the damping device and a rear guide bush disposed downstream of the damping device, the guide bush being adapted for guiding the elongated object through the damping device.

15. Guide device according to claim 14, wherein at least one of the front guide bush and the rear guide bush defines an axial passage opening for the elongated object, wherein the axial passage opening has an inlet side which is widened in funnel-shaped manner.

16. Guide device according to claim 14, wherein at least one of the front guide bush and the rear guide bush is essentially made from hard metal.

17. Guide device according to claim 14, wherein at least one of the front guide bush and the rear guide bush define a passage opening which is highly polished at least in the area through which passes the elongated object.

18. Guide device according to claim 14, wherein the front guide bush and the rear guide bush have an identical construction.

19. Guide device according to claim 1, wherein the guide device has a sleeve-like casing and at least one of a front guide bush disposed upstream of the damping device and a rear guide bush disposed downstream of the damping device and wherein at least one of the front guide bush and the rear guide bush is detachably fixed to the sleeve-like casing.

20. Guide device according to claim 14, wherein the damping device is fixed in clamping manner between the front guide bush and the rear guide bush.

21. Guide device according to claim 14, wherein the damping device is symmetrically arranged between the front guide bush and the rear guide bush.

22. Test device for testing wires and other elongated objects in a continuous process in which an elongated object passes at high speed through the test device in a passage direction along a passage axis, the test device comprising an axial test section in which is located at least one test probe for testing the elongated object while transiting the test device, wherein in at least one location upstream and downstream of the axial test section in the passage direction is provided at least one guide device, the guide device comprising a damping device for damping vibrations of the transiting elongated object, wherein the damping device has a plurality of elastic damping members adapted for contacting the object passing through the damping device.

23. Test device according to claim 22, wherein the test device is adapted for magnetic, non-destructive testing of the elongated objects.

24. Test device according to claim 22, wherein the test probe comprises an eddy current probe.

25. Test device according to claim 22, wherein between a test probe located in the test section and the guide device there is an axial spacing with a length of less than 10 mm.

26. Test device according to claim 25, wherein the axial spacing is between 0.5 and 2 mm.

27. Guide device for guiding elongated objects, which are movable in a passage direction along a passage axis relative to the guide device, the guide device comprising a damping device for damping vibrations of the elongated objects when transiting the guide device, wherein the damping device has a plurality of substantially more than ten elastic damping members adapted for contacting the elongated objects passing through the guide device.

28. Guide device for guiding elongated objects, which are movable in a passage direction along a passage axis relative to the guide device, the guide device comprising a damping device for damping vibrations of the elongated objects transiting the guide device, wherein the damping device comprises a brush arrangement with a plurality of elastic damping members adapted for contacting the elongated objects passing through the guide device, the damping members being formed by brush fibers of the brush arrangement.

* * * * *